United States Patent [19]

Bode et al.

[11] Patent Number: 4,930,350
[45] Date of Patent: Jun. 5, 1990

[54] ACOUSTICAL LENGTH MEASUREMENT

[76] Inventors: Robert Bode, 14545 Bammel St., No. Houston Apt. #1205, Houston, Tex. 77014; Harlan L. Nicholson, 804 First Ave., Harvey, La. 70058

[21] Appl. No.: 254,222

[22] Filed: Oct. 6, 1988

[51] Int. Cl.⁵ ............................................. G01N 29/04
[52] U.S. Cl. ...................................... 73/597; 367/902
[58] Field of Search ...................... 73/597, 598, 602; 367/99, 108, 115, 127, 128, 902, 908

[56] References Cited

U.S. PATENT DOCUMENTS 4,494,224 1/1985 Morrell et al. ...................... 367/115
4,584,676 4/1986 Newman ................................ 73/597

*Primary Examiner*—Hezron E. Williams
*Assistant Examiner*—Louis M. Arana
*Attorney, Agent, or Firm*—George A. Bode

[57] ABSTRACT

An apparatus and method for measuring the length of a tubular body. The apparatus comprises: a transmitter (10) positioned at first end of the tubular body (12) for transmitting an acoustical signal along the interior of the body (12), a reflecting medium (14) provided at the other end of the body (12) for reflecting the transmitted acoustical signal, acoustical receivers (26, 28) for measuring the period of time for the signal to be transmitted along the body (12) from the transmitter (10) to the second end of the body (12) and be reflected back to the first end, acoustical receivers (26, 28) provided along the central axis of the body (12) for measuring the speed of sound therein, and, circuitry (42, 44) for calculating and displaying the length of the body (12) as a function of the period of time and speed of sound in the body (12). The method comprises the steps of: pre-selecting an acoustical signal at a frequency at or below the "cut on" frequency of the body (12), transmitting the signal along the interior of the body (12) from the transmitter (10) positioned at the first end to the reflector (14) positioned at the other end and back again to the transmitter (10), measuring the period of time for the signal to be transmitted along the body (12) from the transmitter (10) to the other end (14) of the body (12) and be reflected back to the first end, measuring the speed of sound provided along the central axis of the body (12), and, calculating the length of the body (12) as a function of the period of time and the speed of sound in the body (12).

15 Claims, 4 Drawing Sheets

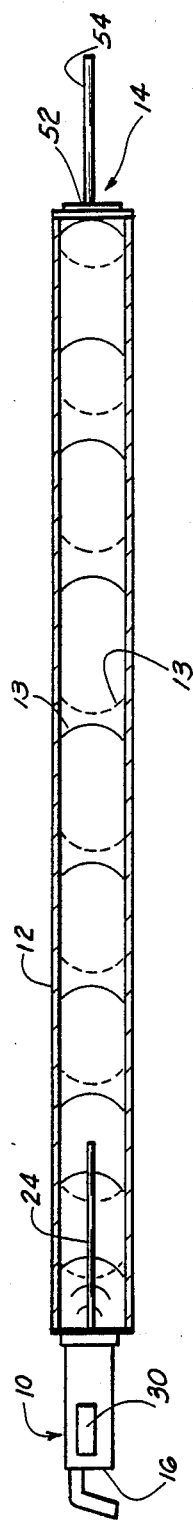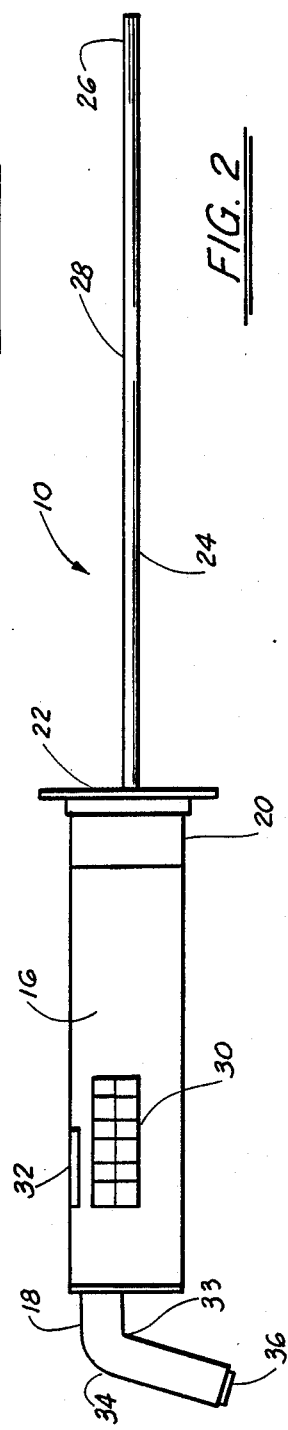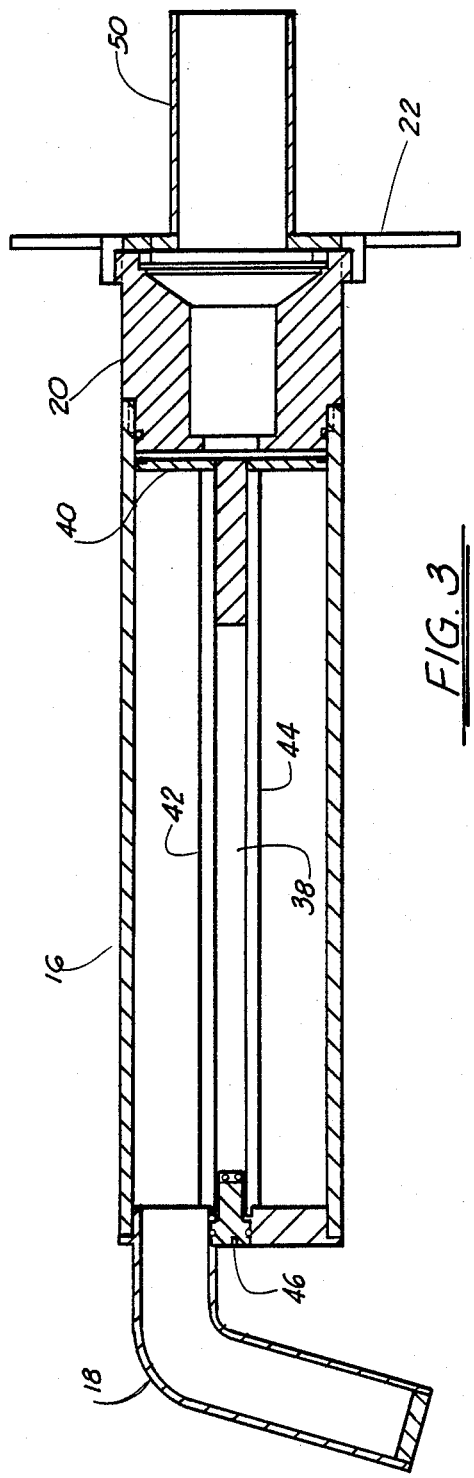

ACOUSTICAL LENGTH MEASUREMENT

The present invention relates to measurement of the length of tubular bodies such as pipes or the like by reflection of acoustic signals. The examples described herein are particularly concerned with the measurement of drill pipe and tubular casings in the oil industry, however, the invention is equally applicable in other fields requiring accurate measurement of tubular bodies.

There is a requirement in the oil industry, and in numerous other fields, to determine the lengths of tubular bodies within close tolerances. In the oil industry, tubes to be measured may vary in length from seventeen to forty-seven feet (5.2 to 14.3 m), or multiples thereof, and at present are measured using steel tape and a forklift or crane to handle the tube. This requires three or more persons (two to handle the tape, a crane or forklift operator and possibly a fourth to record data) and the best accuracy obtainable is $\frac{5}{8}"$ to $\frac{3}{4}"$ (1.6 cm to 1.9 cm) in a forty-seven foot (14.3 m) length. Errors arise from misalignment and misreading of the tape, allowing the tape to sag, and failure to correct for thermal expansion of the tape. Manual recording and transcribing of data leads to further errors. This method of measurement is thus costly due to the inherent errors, the numbers of personnel and equipment required, and the risk of physical injury.

Accordingly, there is a requirement for an accurate, reliable method of measuring tube lengths, requiring fewer personnel and mitigating any errors.

Possible solutions to this problem include pulsed light and laser methods, however, these are restricted to line of sight applications and any bow in the tube will introduce an error, or, if the bow is great enough, make measurement impossible. Radar methods would not be restricted to line of sight, however a radar signal would have to be tuned to the tube diameter and the equipment required would be too bulky for portable use.

A further alternative is the use of acoustic signals. An acoustic wave will propogate down the inside of a tube in a similar manner to high frequency radio waves giving a potentially accurate measurement of curved tubes, and electro-acoustic devices have been developed for this purpose. These have not met with widespread acceptance, however, due to their lack of accuracy and repeatability. The inaccuracy in such devices arises from factors such as variations in the speed of sound in the operating environment and difficulties in measuring the travel time of the acoustic signal. The speed of sound in a tube varies with the temperature, humidity and density of the medium in the tube, and the diameter, shape and wall conditions of the tube itself, and measurement of the travel time is affected by "spiralling" of the acoustic wave within the tube, inaccuracies in signal detection, and phase shifts occuring during the propogation of the wave and in the associated electronic components.

Existing systems have been improved by the addition of circuitry for sensing temperature and pressure and to correct for the tube diameter so as to obtain a more accurate value for the speed of sound upon which length calculations can be based, however such equipment is relatively complex and expensive and still does not achieve the required levels of accuracy and repeatability.

It is an object of the present invention to obviate or mitigate the aforesaid disadvantages of existing measurement techniques. A further object of the invention is to provide a portable, reliable and accurate measurement apparatus which may operate in an oilfield environment.

In accordance with a first aspect of the invention, a method of measuring the length of a tubular body comprises the steps of transmitting an acoustic signal along the interior of the tubular body using acoustic transmitter means, located at one end of the tubular body, measuring the time taken for the signal to be transmitted along the tubular body and reflected back using acoustic receiver means, and calculating the length of the tubular body from the time of travel of the signal and the speed of sound, wherein the frequency of the signal is set at or below the cut on frequency for the diameter of the tubular body being measured.

Preferably, the speed of sound in the tubular body is measured by means of first and second acoustic receiver means displaced from one another along the central axis of the tubular body.

Preferably also, the first and second acoustic receiver means are located within the tubular body adjacent the end thereof where the acoustic transmitter means is located, and the receiver means nearest said end is positioned at least one quarter wavelength of the signal inwardly from said end.

Preferably also, the time of travel of the signal is measured from the instant at which the transmitted signal passes said first receiver means to the instant that the reflected signal is detected by said first receiver means, and the distance between the first receiver means and the end of the tube from which the signal was transmitted is added to the length calculated from the time of travel of the signal.

Preferably also, the signal is a single cycle wave and the time of travel of the signal is measured from the zero crossing points of said wave.

Preferably also, the calculated length is corrected to compensate for phase shifts occuring during reflection of the signal and for the response characteristics of the acoustic receiver means.

Preferably also, the gains of the acoustic receiver means are adjusted between detection of the transmitted and reflected signals to compensate for attenuation of the reflected signal.

According to a second aspect of the invention, apparatus for acoustic length measurement of a tubular body comprises means for transmitting an acoustic signal, means for locating said transmitter at a first end of a tubular body, acoustic receiver means located forwardly of said transmitter means, and data processing means connected to said acoustic receiver means.

Preferably, the frequency of the signal is set at or below the cut on frequency for the diameter of the tubular body.

Preferably also, a second acoustic receiver means in provided between said transmitter means and said first receiver means.

Preferably also, said second receiver means is positioned at a distance from the transmitter means such that, in use, it is located at least one fourth wavelength of the signal inwardly from said first end of the tubular body.

Preferably also, said first and second receiver means are mounted on an elongate member which, in use, projects into the tubular body and extends along the central axis thereof.

Preferably also, the probe is formed from a material having a relatively low coefficient of linear thermal expansion.

Preferably also, the apparatus includes microprocessor means for controlling the transmitted signals and for processing and storing data.

Preferably also, said transmitter and locating means are interchangeable, allowing the apparatus to be adapted for use with tubular bodies of different diameters.

Preferably also, the apparatus further includes reflector means locatable at the second, opposite end of the tubular body.

The apparatus is also preferably provided with a keypad or other data input device, visual display means and a data port for downloading stored data.

An embodiment of the invention will now be described, by way of example only, with reference to the accompanying drawings in which, FIG. 1 is a side view of apparatus embodying the invention in use with a tubular body, shown in section;

FIG. 2 is a side view of a hand held unit forming part of the apparatus of FIG. 1;

FIG. 3 is a sectional side view of the unit of FIG. 2 adapted for use with a smaller diameter tube;

Figure 4:
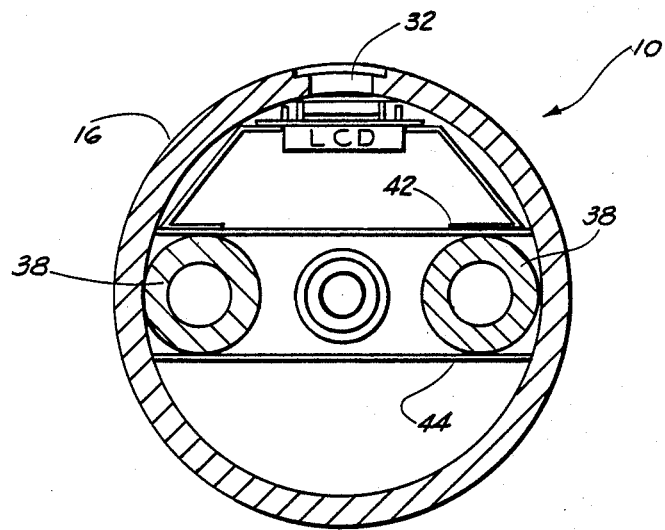
FIG. 4 is a sectional end view of the unit of FIG. 2.

Referring now to the drawings, FIG. 1 shows an acoustic length measuring unit 10 applied to one end of a length of tubing 12, and a reflector 14 applied to the opposite end, the length of the pipe being measured by means of an acoustic pulse transmitted from the unit 10, the time taken for the pulse to travel along the tubing 12 and be reflected back to the unit 10 being measured such that length of the tubing may be derived from the measured time and the velocity of sound.

As is best seen in FIGS. 2 to 4, the unit 10, which is designed for hand held use, comprises a generally tubular housing body 16 closed at its rearward end by a rear end cap and handle assembly 18 and at its forward end by a loudspeaker housing 20. A circular reference plate 22, corresponding in size to the diameter of the tubing to be measured, is affixed to the forward end of the loudspeaker housing 20 and an elongate probe 24 extends forwardly along the central long axis of the housing body 16. First and second microphones 26 and 28 are mounted on the probe 24, the first, 26, adjacent the forward end thereof and the second, 28, rearwardly of the first and a known distance therefrom. The housing body 16 is provided with a keypad 30 for inputting data and instructions and an LCD visual display unit 32. The handle 18 includes a trigger 33, a store key 34 and a data input/output port 36.

As shown in FIGS. 3 and 4, the housing body 16 contains tubular battery holders 38 extending along either side thereof between the rear end cap 18 and a forward fixing plate 40, and first and second circuit boards 42 and 44 mounted above and below the battery holders 38. The unit may be powered by re-chargeable batteries (not shown) and the holders 38 are accessible via closure caps 46.

Figure 5:
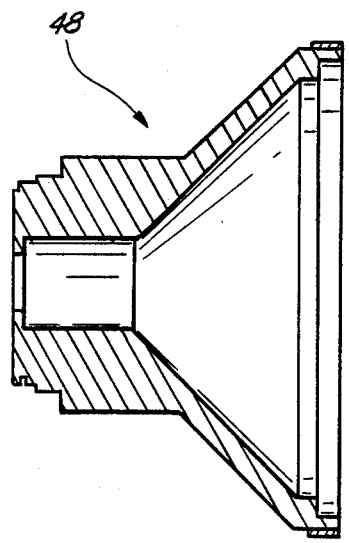
FIG. 5 is a sectional side view of a loudspeaker housing for use with the unit of FIG. 2.

The loudspeaker housing 20 is a screw-fit onto the forward end of the housing body 16 and is interchangeable with differently sized loudspeaker housings such as 48 (FIG. 5). Interchangeable reference plates 22 are threadably attachable to the forward end of the speaker housing 20. Alternatively, a bore reduction sleeve 50 may be fitted, allowing the unit 10 to be used with smaller pipes. The present example is particularly concerned with oilfield applications and is intended to be used with tubes varying from 2" (5.08 cm) to 20" (50.8 cm) internal diameter. Two loudspeaker housings 20 and 48, mounting 3" (7.62 cm) and 8" (20.32 cm) loudspeakers respectively, are sufficient to cover this range in combination with a suitable range of reference plates 22 and bore reduction sleeves 50, the 3" (7.62 cm) loudspeaker housing 20 being used for tubes up to 8" (20.32 cm) diameter and the 8" (20.32 cm) loudspeaker housing 48 for tubes from 8" (20.32 cm) to 20" (50.8 cm) diameter. The reflector 14 comprises a flat circular plate 52 having a detachable handle 54 attached thereto, and may be provided in a corresponding range of sizes.

Figure 6:
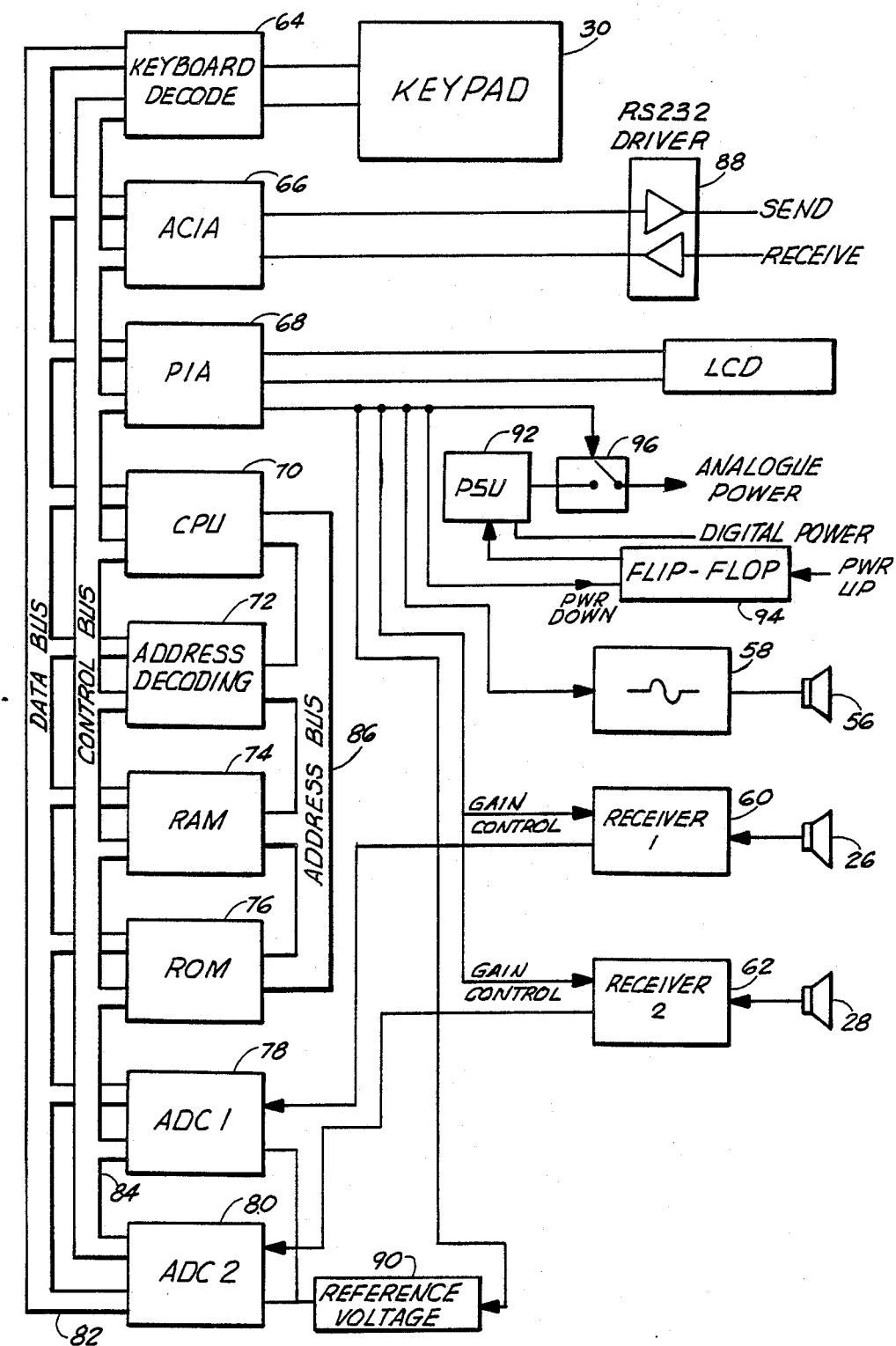
FIG. 6 is a block diagram of the elctronic circuitry of the unit of FIG. 2.

FIG. 6 is a block diagram of the analogue and digital hardware of the unit 10. The analogue hardware includes a main acoustic transducer (loudspeaker) 56, a wave form generator/power amplifier 58 which drives the transducer 56, the first and second microphones 26 and 28, and associated variable gain amplifiers 60 and 62. The digital hardware is based on a CMOS 6809 8-bit microprocessor and includes a keyboard decoder 64, an access control interface adapter (ACIA) 66, a peripheral interface adapted (PIA) 68, a central processing unit (CPU) 70, and address decoder 72, 32k random access memory (RAM) 74, 32k erasable programmable read only memory (EPROM) 76 and first and second analogue to digital converters (ADC 1 and ADC 2) 78 and 80, interconnected as shown by data, control and address buses 82, 84 and 86.

The keyboard decoder 64 is connected to the keypad 30, and the ACIA 66 to the data port 36 via an RS232 driver 88. The PIA 68 is connected to the LCD display 32 and also to the waveform generator/power amplifier 58 and the gain controls of the variable gain amplifiers 60, 62. The outputs of the amplifiers 60, 62 are connected to the ADC's 78 and 80 respectively and the PIA 68 further serves to control a switchable reference voltage 90 for the ADC's 78 and 80. A power supply unit (PSU) 92 powers both the digital and analogue hardware and is controlled by a flip-flop 94 which is powered up by depressing the trigger 33 and powered down by the CPU 70 via the PIA 68, which also controls a switch 96 to control independently the power supply to the analogue hardware. The programming of the microprocessor is arranged to power down the PSU 92 if idle for more than a predetermined time.

As will be described in more detail below, the physical design and method of operation of the unit 10 serves to eliminate or minimise the various factors which contribute to the lack of accuracy in acoustic length measurement.

The first consideration is controlling the frequency of the acoustic pulse to ensure substantially undistorted plane wave propogation along the tube 12. The wave 13 will begin to "spiral" inside the tube 12, thus erroneously increasing the measured travel time, if the frequency of the pulse exceeds a certain cut on frequency (c.o.f.) which is related to the diameter of the tube 12 by the expression:

$$c.o.f. = (1.84 \times C_0)/(\pi D);$$

where Co is the speed of sound in free air and D is the internal diameter of the tube 12. Thus, the cut on frequency for a 2" (5.08 cm) tube is 3821 HZ and for a 20" (50.08 cm) tube is 382 HZ. Any frequency below the cut on frequency should give proper plane wave propogation, however for safety the frequency should be set at least 10% below cut on for a given tube diameter. The frequency may thus be tuned to suit the diameter of the tube 12 being measured, however it will be appreciated that the frequency may simply be set at a value lower than the cut on frequency for the largest tube of interest and that this frequency will also be suitable for all smaller tubes. Thus, in the present example the frequency is set at 300 HZ which will provide proper plane wave propogation in all tubes of 20" (50.8 cm) diameter or less. In this example each pulse is a single cycle sine wave produced by the waveform generator 58 and whose parameters are determined by data stored in the EPROM 76. The waveshape may thus be altered by changing the stored data.

A second major source of error in acoustic measurement techniques arises from variations in the speed of sound in the operating environment. As previously noted, the speed of sound in a tube is affected by the temperature, humidity and density of the medium within the tube as well as by the physical characteristics of the tube. The relationships of the speed of sound to temperature and tube diameter are known and may be measured, allowing the speed of sound to be corrected for use in calculating the length of a tube, however such measurements may be inaccurate and increase the complexity of the device. Other factors are not readily measured and their effect on the speed of sound is not easily determined.

In the present case these problems are overcome by measuring the actual speed of sound in the tube 12 during the length measurement process. This is achieved by means of the two microphones 26 and 28 which are displaced from one another along the central axis of the tube 12 by a known distance. The speed of sound in the actual operating environment may thus be determined by measuring the time taken for the acoustic pulse to travel between the microphones 26 and 28.

A further source of error is the acoustic impedance mis-match arising from differences in the sizes of the loudspeaker 56 and the tube 12, which results in a phase shift occuring in the acoustic pulse upon injection into the tube 12. It has been found that this phase effect may be eliminated if the microphone 28 nearest the loudspeaker housing 20 is positioned at least a quarter wavelength from the end of the tube 12 to which the unit 10 is applied. Where the diameter of the tube 12 varies near its ends (as with a tapered thread on a drill pipe), this distance is preferably increased somewhat and may typically be 14" (35.56 cm) with a 300 HZ pulse.

The first microphone 26 is also set slightly back from the forward end of the probe 24 to minimise the effect of any distortion of the reflected pulse which might occur when it strikes the end of the probe 24.

A phase shift in the pulse may also occur upon reflection of the pulse from the reflector 14, and may be eliminated either by using a material which does not produce a phase shift (such as ½" (1.27 cm) stainless steel) or by determining the phase shift produced by the reflector material, such as aluminium, and applying a correction to the measured length.

Further inaccuracies in the measured length of the tube arise from errors in measuring the travel time of the pulse. One such error arises if the pulse is timed from the loudspeaker 56 actually being triggered to the reflected pulse being detected by the first microphone 26, due to the response time of the loudspeaker 56 etc. This may be avoided by timing the pulse from the instant the transmitted pulse passes the microphone 26 to the instant when the reflected pulse is detected. Correction factors may be applied to measured times to compensate for the response times of the microphones 26 and 28.

Timing errors may also be caused by difficulties in clocking the same point on the pulse waveform on transmission and reflection. Level detection introduces errors due to attenuation of the reflected pulse, whilst with peak detection, which is potentially more accurate, difficulties are encountered in detecting peaks in the relatively low frequency waves required in larger tubes, this being further exacerbated by the attenuation of the pulse tending to flatten the peak. Accordingly, the present example utilises zero crossing detection comprising subsequent low—and high—resolution analysis to detect the zero crossing points on which the travel time of the pulse is based. It is also desirable to adjust the gains of the microphone amplifiers 60, 62 between detection of the transmitted and reflected pulses so as to compensate approximately for the attenuation of the reflected pulse. Suitable gain values may be set up by means of a series of test pulses fired prior to the actual measurement process taking place.

Phase shifts in the electronic components of the units themselves present a further source of potential error and may be avoided by careful design. For example, the use of a buffered attenuator in controlling the gain settings of the microphone amplifiers 60, 62 will eliminate phase shifts which might arise with the more conventional method of altering feedback components.

It is also important that the distance between the two microphones 26, 28 varies as little as possible, so as to preserve the accuracy of the measured speed of sound and the overall length measurement (which requires the known distance between the first microphone 26 and the reference plate 22 to be added to the distance calculated from the first microphone to the reflector 14). Accordingly, the probe 24 should be formed from a material which has as low coefficient of thermal linear expansion as possible whilst being sufficiently strong to withstand use in an oilfield environment, bearing in mind that its cross sectional area should also be as small as is practicable. Suitable materials include stainless steel and cast nylon.

Figure 7:
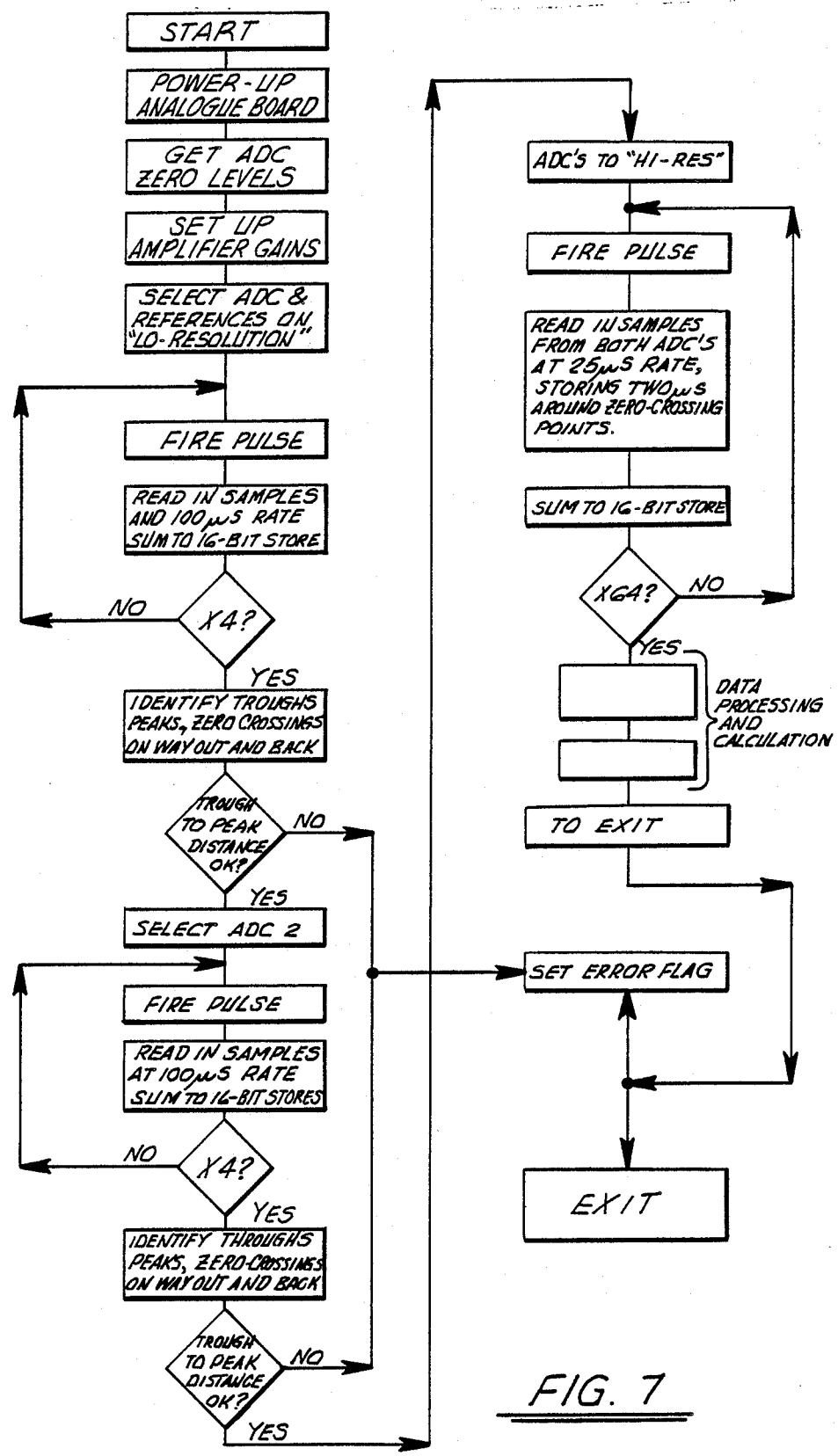
FIG. 7 is a flow diagram illustrating the method of operation of the apparatus of FIGS. 1 to 6.

FIG. 7 is a flow diagram illustrating the detailed operation of the system once the trigger 33 is depressed. Once the circuitry is powered up, a series of test pulses is fired to set up the gains of the microphone amplifiers 60, 62. AC 1 (78) is then selected and a series of four pulses fired for low resolution analysis. For each pulse the transmitted and reflected waves are sampled at a relatively low sampling rate (eg. 100 μs intervals) and the data for the four pulses averaged to give approximate values for the troughs, peaks and zero-crossings. The peak to trough distances are then checked and an error flag set if any anomalous value is detected. This process is repeated with ADC 2 (80). A higher resolution analysis is then carried out wherein a series of sixty four pulses are fired, each being sampled at a higher sampling rate (eg. 25 μs intervals), and the samples around the approximate zero-crossings previously determined are stored. This data is then used to determine accurate zero-crossing points wherefrom the speed of sound and the length of the tube 12 may be calculated. The calculated length measurement may be displayed on the LCD display 32, indexed using the keypad 30 and stored by depressing the store key 34. Accumulated data may be downloaded to a computer, hardcopy printer or other storage medium via the data port 36.

The various features of the unit 10 and the measuring method described above all contribute to enhancing the accuracy and repeatability of acoustic length measurement whilst allowing the unit 10 to be relatively compact. In this example, accuracy in the order of plus or minus ⅛" (3.2 mm) in 100 feet (30.48 m) is achievable. The measurement process is also greatly simplified and accelerated, requiring two persons at most, and the possibility of human error in recording data is also eliminated. It should be noted also that the use of the reflector 14 is not strictly necessary. In the oil industry, for example, drill pipe may be measured whilst racked in a pipe stand by determing the reflection phase shift of the material from which the deck of the stand is made (typically oak wood), using the deck of the stand as a reflector and applying an appropriate correction to the time of travel of the pulse. A reflected pulse will also be obtained in an open ended tube (with a phase shift requiring a time correction dependent upon the tube diameter), so that it is feasible that measurements may be obtained without the use of any reflector at all. In this case, of course, the attenuation of the reflected pulse would be significantly greater.

It will be appreciated that the various features of the physical design of the measuring instrument and the method of use are equally applicable in numerous fields outside the oil industry.

What is claimed as invention is:

1. An apparatus for measuring the length of a tubular body comprising:
   a. means for transmitting an acoustical signal along the interior of said tubular body, said transmitting means being positioned at the first end of said tubular body, closure means being provided at said first end of said tubular body;
   b. means provided at the other end of said tubular body for reflecting said transmitted acoustical signal;
   c. means for measuring the period of time for said acoustical signal to be transmitted along said tubular body from said transmitting means to the other (second) end of said tubular body and be reflected back to said first end thereof;
   d. a plurality of acoustical receiving means mounted on an elongated probe extending from said enclosure means and provided along the central axis of said tubular body for measuring the speed of sound therein, said first acoustical receiving means being positioned in said tubular body forward of and adjacent to said acoustical transmitting means; and,
   e. means connected to said measuring means and said acoustical receiving means for calculating the length of said tubular body as a function of said period of time and the speed of sound in said tubular body.

2. The apparatus of claim 1, further comprising means connected to said calculating means for visually displaying said length of said tubular body.

3. The apparatus of claim 1, wherein said acoustical signal is a single cycle acoustic signal.

4. The apparatus of claim 1, wherein the first of said acoustical receiving means is positioned adjacent said acoustical transmitting means.

5. The apparatus of claim 4, wherein said second of said acoustical receiving means is positioned intermediate said transmitting means and said first acoustical receiving means and is spaced at least a distance equal to one-fourth (¼) of the wavelength of said signal and inwardly of said first end.

6. An apparatus for measuring the length of a tubular body comprising:
   a. means for transmitting a single cycle acoustical signal along the interior of said tubular body, said transmitting means being positioned at the fist end of said tubular body, closure means being provided at said first end of said tubular body;
   b. means provided at the other end of said tubular body for reflecting said transmitted acoustical signal;
   c. means for measuring the period of time for said acoustical signal to be transmitted along said tubular body from said transmitting means to the other (second) end of said tubular body and be reflected back to said first end thereof;
   d. a plurality of acoustical receiving means mounted on an elongated probe extending from said closure means and provided along the central axis of said tubular body for measuring the speed of sound therein, said first acoustical receiving means being positioned in said tubular body forward of and adjacent to said acoustical transmitting means, and wherein said second of said acoustical receiving means is positioned intermediate said transmitting means and said first acoustical receiving means and is spaced at least a distance equal to one-fourth (¼) of the wavelength of said acoustical signal and inwardly of said first end;
   e. means connected to said measuring means and said acoustical receiving means for calculating the length of said tubular body as a function of said period of time and the speed of sound in said tubular body; and,
   f. means connected to said calculating means for visually displaying said length of said tubular body.

7. A method for measuring the length of a tubular body having closure means provided at one end thereof comprising:
   a. pre-selecting an acoustical signal at a frequency at or below the cut on frequency of said tubular body;
   b. transmitting said acoustical signal along the interior of said tubular body from a transmitting means positioned at the first end of said tubular body to a means for reflecting said signal positioned at the other (second) end thereof and back again to said transmitting means;
   c. measuring the period of time for said acoustical signal to be transmitted along said tubular body from said transmitting means to said other (second) end of said tubular body and be reflected back to said first end thereof;
   d. measuring the speed of sound by a plurality of acoustical receiving means mounted on an elongated probe extending from said closure means and positioned along the central axis of said tubular body and forward of and adjacent to said acoustical transmitting means, wherein the first of said acoustical receiving means is positioned adjacent said acoustical transmitting means and the second of said acoustical receiving means is positioned intermediate said transmitting means and said first acoustical receiving means and spaced at least a distance equal to one-fourth (¼) of the wavelength of said signal inwardly of said first end; and, e. calculating the length of said tubular body as a function of said period of time and the speed of sound in said tubular body.

8. The method of claim 7, further comprising the step of visually displaying said calculated length of said tubular body.

9. The method of claim 7, wherein said acoustical signal is a single cycle acoustical signal.

10. The method of claim 7, further comprising the step of correcting said calculated length to compensate for phase shifts occurring during reflection of said signal and the response characteristic of said acoustical receiving means.

11. The method of claim 7, further comprising the step of adjusting the gains of said acoustical receiving means at a time between detection of the transmitted signals and reflection thereof.

12. A method for measuring the length of a tubular body having a closure means at one end thereof comprising:

a. pre-selecting a single cycle acoustical signal at a frequency at or below the cut on frequency of said tubular body;

b. transmitting said acoustical signal along the interior of said tubular body from a transmitting means positioned at the first end of said tubular body to a means for reflecting said signal positioned at the other (second) end thereof and back again to said transmitting means;

c. measuring the period of time for said acoustical signal to be transmitted along said tubular body from said transmitting means to said other (second) end of said tubular body and be reflected back to said first end thereof;

d. measuring the speed of sound by a plurality of acoustical receiving means, said means being mounted on an elongated probe extending from said closure means and positioned in said tubular body along the central axis thereof and forward of and adjacent to said acoustical transmitting means, wherein the first of said acoustical receiving means is positioned adjacent said acoustical transmitting means;

e. calculating the length of said tubular body as a function of said period of time and the speed of sound in said tubular body; and, f. visually displaying said calculated length of said tubular body.

13. The method of claim 12, wherein the second of said acoustical receiving means is positioned intermediate said transmitting means and said first acoustical receiving means and spaced at least a distance equal to one-fourth (¼) of the wavelength of said signal inwardly of said first end.

14. The method of claim 12, further comprising the step of correcting said calculated length to compensate for phase shifts occurring during reflection of said signal and the response characteristic of said acoustical receiving means.

15. The method of claim 14, further comprising the step of adjusting the gains of said acoustical receiving means at a time between detection of the transmitted signals and reflection thereof.

* * * * *